United States Patent [19]

Cure et al.

[11] Patent Number: 5,421,215
[45] Date of Patent: Jun. 6, 1995

[54] IMMERSION SAMPLER FOR MOLTEN METALS WITH REDUCED AREA SLIT-SHAPED INLET

[75] Inventors: Omer P. I. Cure, Diepenbeek, Belgium; Paul C. H. Bernard, LS Meerssen, Netherlands

[73] Assignee: Heraeus Electro-Nite International N. V., Houthalen, Belgium

[21] Appl. No.: 12,559

[22] Filed: Feb. 2, 1993

[30] Foreign Application Priority Data

Feb. 19, 1992 [DE] Germany .................. 42 04 952.0

[51] Int. Cl.$^6$ ............................................. G01N 1/12
[52] U.S. Cl. .............................. 73/864.53; 73/864.59; 73/DIG. 9
[58] Field of Search ........... 73/864.51, 864.52, 864.53, 73/864.54, 864.55, 864.56, 864.57, 864.58, 864.59, DIG. 9

[56] References Cited

U.S. PATENT DOCUMENTS

| | | | |
|---|---|---|---|
| 3,332,288 | 7/1967 | Mladenovich | 73/864.52 |
| 3,604,270 | 9/1971 | Falk . | |
| 4,116,070 | 9/1978 | Falk | 73/864.57 |
| 4,453,424 | 6/1984 | Hackett . | |
| 5,033,320 | 7/1991 | Bearts . | |

FOREIGN PATENT DOCUMENTS

| | | | |
|---|---|---|---|
| 665485 | 6/1965 | Belgium . | |
| 0362414 | 4/1990 | European Pat. Off. . | |
| 1526144 | 5/1968 | France . | |
| 1266024 | 4/1968 | Germany . | |
| 1648954 | 7/1971 | Germany . | |
| 2406764 | 9/1974 | Germany . | |
| 3008061 | 9/1980 | Germany . | |
| 1274618 | 5/1972 | United Kingdom | 73/864.55 |
| 1429106 | 3/1976 | United Kingdom . | |

Primary Examiner—Richard E. Chilcot, Jr.
Assistant Examiner—Joseph L. Felber
Attorney, Agent, or Firm—Panitch Schwarze Jacobs & Nadel

[57] ABSTRACT

Immersion samplers for the molten metals have a tubular sample chamber made of quartz glass or another refractory material with an inlet opening on the one end and an end, lying opposite to the inlet opening, which is mounted in a cardboard tube. An immersion sampler with a simple construction which makes possible sampling at low metal inlet velocity while preventing the formation of pinholes and pores in the sample, comprises an inlet opening for filling the sample chamber exclusively by ferrostatic pressure, the inlet having an open cross-sectional area compared to the cross-sectional area of the sample chamber directly behind the inlet opening, looking counter to the immersion direction, which is so sized that the filling velocity of the sample chamber based on ferrostatic pressure is at a maximum one fifth of the filling velocity at an inlet opening corresponding to the cross sectional area of the sample chamber directly behind the inlet opening. The inlet opening is also arranged in such a way that the incoming melt flows in at an angle greater than 0° to the longitudinal axis of the sample chamber.

7 Claims, 2 Drawing Sheets

IMMERSION SAMPLER FOR MOLTEN METALS WITH REDUCED AREA SLIT-SHAPED INLET

FIELD OF THE INVENTION

The invention relates to an immersion sampler for molten metals with a small diameter tubular sample chamber made of quartz glass or of a refractory material with an inlet opening on one end, and where the end of the sample chamber which lies opposite to the inlet opening is mounted a cardboard tube.

BACKGROUND OF THE INVENTION

Such an immersion sampler is known from DE-OS 24 06 764. The immersion sampler described therein is used to determine the gas content of a molten metal. It has a sample chamber which lies in front of an additional chamber in which pressure regulation takes place by means of an inert gas stream. The inlet velocity of the molten metal into the sample chamber is thereby regulated. In addition, a gas inlet and a vacuum chamber are connected through valves to the ante-chamber of the immersion sampler, so that the pressure can be either increased or decreased, as desired, in the immersion sampler. By regulating the pressure in this way, the time of entry of the molten metal into the sample chamber is selected so that entry of slag into the testing chamber is prevented. In the area of inlet of the melt into the sample chamber there is a narrowing which effectuates a closing of the sample chamber after successful sampling, by means of the molten metal quickly solidifying at this location. Immersion samplers of this type are expensive, since they require means for the supply as well as evacuation of gases, in order to make pressure regulation possible. In order to enable the gas flow to bypass the sample chamber, such immersion samplers have a relatively complicated structure at their immersion end.

Another immersion sampler is known from DE-AS 12 66 024. According to this reference, the regulation of gas pressure in the sample chamber takes place by means of a piston-cylinder arrangement. By this pressure regulation the inlet velocity of the molten metal into the testing chamber is regulated, so that the development of pinholes or bubbles in the sample is avoided. This type of immersion sampler also has a high apparatus cost.

In view of the above prior art, it is the object of the present invention to produce an immersion sampler for molten metals, whose simple construction makes possible a sampling with low inlet velocity and with prevention of formation of pinholes and pores in the sample.

SUMMARY OF THE INVENTION

According to the invention the problems of immersion samplers with the above-described characteristics are solved in that for the filling of the sample chamber, exclusively by ferrostatic pressure, the inlet opening has an open cross-section in comparison to the cross-section of the sample chamber directly behind the inlet opening, looking counter to the immersion direction, the size of which is so chosen that the filling velocity of the sample chamber based on the ferrostatic pressure is at a maximum one fifth of the filling velocity at an inlet opening corresponding in size to the cross-section of the sample chamber in the area behind the inlet opening, and that the inlet opening is so arranged that the incoming melt flows in at an angle greater than 0° to the longitudinal axis of the sample chamber. Through such a reduction of the filling velocity with simple construction means, the melt flows into the sample chamber without spattering. Thereby the sample chamber is filled very evenly with the molten metal, so that the development of pinholes and pores is avoided. The sample therefore develops a very smooth surface.

The inlet opening can, for purposes of simplicity, be created by sawing or milling, so that it is slit-shaped. For an even inlet flow, an arrangement of this slit-shaped inlet opening which is perpendicular to the longitudinal axis of the sample chamber has proven to be suitable. However, it is also possible to form the inlet opening in the shape of a bore, for example.

Through the lateral arrangement of the inlet opening, according to the invention, the danger is reduced of intrusion of impurities, for example eventual particles of a possible cap which may protect the sample chamber during the immersion of the immersion sampler into the molten metal. With such an immersion sampler it is not only possible to determine the gas content of molten metals, such as the oxygen or nitrogen content, but also, due to the high sample quality, to reproducibly determine with high accuracy the concentration of other elements, such as carbon and sulfur. This would not be the case, if the sampler were contaminated, for example with pinholes. The sample taking and preparation for analysis take only very little time, so that upon changes in the process of the metal production quick adjustments can be made and a high quality of the metal achieved after the melting process.

It has proved advantageous, if the inlet direction makes an angle with the longitudinal axis of the sample chamber of between 30 degrees and 150 degrees, especially an angle of between 80 degrees and 100 degrees, counter to the immersion direction. Thereby the inlet opening will be arranged outside of the crossing point of the longitudinal axis of the sample chamber with the end of the sample chamber, for example on the cylindrical side surface of the tubular sample chamber. With such an arrangement of the inlet opening particles of a destroyed protection cap in the molten metal cannot enter into the sample chamber, but flow past the inlet opening.

For a sufficient reduction of the filling velocity it is advantageous that the open cross-sectional area of the inlet opening be between 0.4 and 3 mm$^2$. Therefore, it is suitable that the smallest opening width of the inlet opening be at least 0.1 mm.

It is also advantageous if the immersion end of the sample chamber is so constructed that it has a narrowing cross section. In particular, this end can be closed by rounding it off. Thereby the flow behavior of the molten metal in the area of the inlet opening during the immersion procedure is improved.

In an advantageous embodiment of the invention the end of the testing chamber, which is opposite the immersion end, has set thereon an open-pored plug or stopper which fills the cross section of the sample chamber. This plug is preferably made of molding sand or silicon carbide, i.e., it is gas permeable but impermeable to the melt. By means of such a gas permeable plug gases can escape from the sample chamber during the filling process of the sample chamber, so that an even filling process, in particular an even filling velocity, is guaranteed.

BRIEF DESCRIPTION OF THE DRAWINGS

The foregoing summary of the invention, as well as the following detailed description of a preferred embodiment, will be better understood when read in conjunction with the appending drawings. For the purpose of illustrating the invention, there is shown in the drawings an embodiment which is presently preferred, it being understood, however, that the invention is not limited to the specific arrangement and instrumentalities disclosed.

DETAILED DESCRIPTION OF PREFERRED EMBODIMENT

Figure 1:
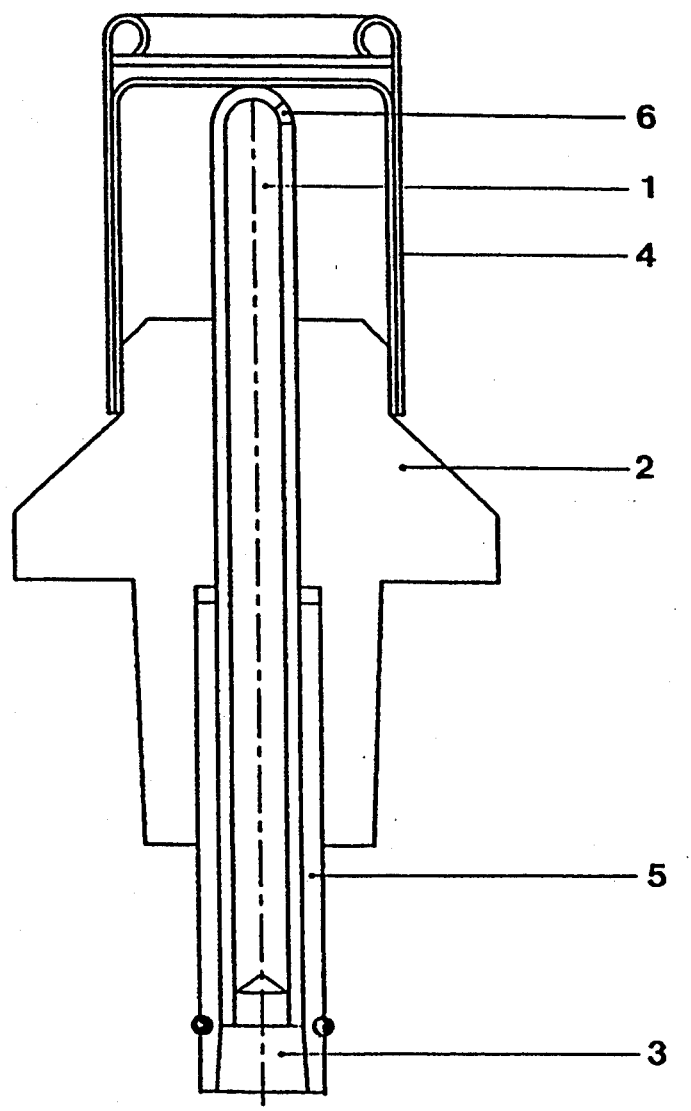
FIG. 1 is a schematic representation of the immersion sampler in cross-section.

The immersion sampler shown in FIG. 1 has a tubular sample chamber 1 which, at its end facing away from the immersion end, is embedded in a rotationally symmetrical molded body 2 made of refractory material, such as molding clay. The molded body 2 serves for the mounting of the sample chamber 1 into a cardboard tube, which is not shown in the drawings. The end of the sample chamber 1 mounted in this manner is closed off with a porous plug 3 of molding sand. The immersion end of the sample chamber is protected by means of a protection cap 4 stuck onto the molded body 2 during the immersion of the immersion sampler into the molten metal. In the molten metal this protection cap 4 is then destroyed, so that the sample chamber 1 comes into contact with the molten metal. At the end which faces away from the immersion end, the sample chamber 1 is additionally surrounded by a metal pipe 5, which increases the stability of the sample chamber 1, and can serve as a gas sealed coupling piece for a lance, which is not shown.

Figure 2:
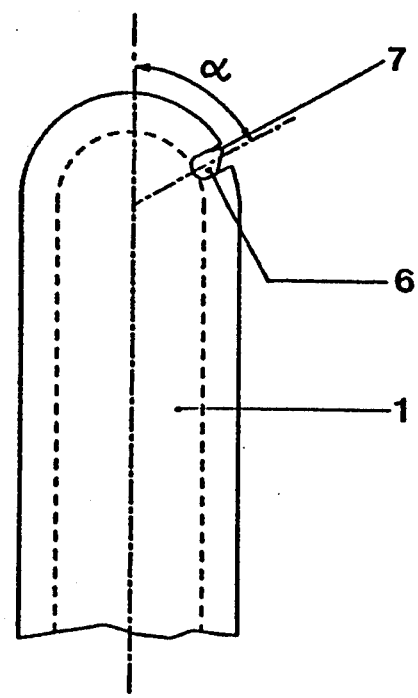
FIG. 2 is a schematic representation of the immersion end of the sampler chamber.
Figure 3:
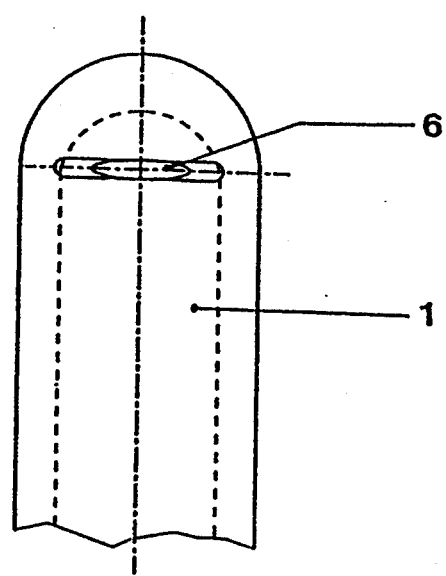
FIG. 3 is a schematic representation of the immersion end of the sample chamber, turned 90 degrees with respect to FIG. 2.

In FIGS. 2 and 3 the immersion end of the sample chamber 1 is displayed with the inlet opening 6. The sample chamber is tubular with an inner diameter of 4 mm and a length of approximately 70 mm. The immersion end of the sample chamber 1 is closed with a curved shape. In the transition area between the curved closure and the cylindrical side wall of the sample chamber the inlet opening is arranged in the form of a slit whose major dimension extends perpendicular (see FIG. 3) to the longitudinal axis of the sample chamber 1. This slit-shaped inlet opening 6 is formed by sawing or milling. It has an open cross-sectional area of approximately 1.5 mm². The smallest opening width of the inlet opening 6 is approximately 0.5 mm.

The inlet direction of the flow of molten metal is determined by the direction of the cut edges 7 of the inlet opening 6 in relation to the longitudinal axis of the sample chamber 1 (see FIG. 2). The cut edges 7 run parallel to each other and form with the immersion direction of the sample chamber 1 an angle $\alpha$ of approximately 80° to 90°, so that the melt runs into the sample chamber 1 counter to the immersion direction.

After destruction of the protection cap 4 the melt flows very slowly through the small, laterally arranged inlet opening 6 into the sample chamber 1 (the filling time is approximately 0.8 seconds; this means that there is a reduction of the filling time by approximately a factor of 9 in comparison to an inlet opening whose cross-sectional area is just as big as the cross-sectional area of the sample chamber, and has a filling time of approximately 0.09 seconds). The flow of the molten metal into the sample chamber 1 therefore occurs very evenly and hence the sample chamber 1 fills up with molten metal which is free of pinholes and pores, whereby after its solidifying a sample with a very smooth surface is created. The lateral arrangement of the inlet opening 6 also prevents fragments of the destroyed protection cap 4 from intruding into the sample chamber 1, since such contamination particles move past the inlet opening 6 as a result of the immersion movement of the immersion sampler.

The wall thickness of the sample chamber 1 is approximately 1 mm. With this thickness the wall has such a high heat capacity in relation to the small inlet opening 6, that the molten metal first solidifies in the inlet opening 6 which is cooler than the molten metal. After heating up of the sample chamber 1, the solidified molten metal in the inlet opening 6 melts and opens the inlet opening 6. This only takes place at a suitable immersion depth of the sampler. At this point in time, the fragments of the protection cap 4, as a result of the immersion movement, are already removed from the area of the inlet opening 6.

The present invention may be embodied in other specific forms without departing from the spirit or essential attributes thereof and, accordingly, reference should be made to the appended claims, rather than to the foregoing specification as indicating the scope of the invention.

1. An immersion sampler for molten metals comprising a tubular sample chamber made of a refractory material with an inlet opening on a first immersion end and a second end, which lies opposite to the inlet opening, characterized in that for filling of the sample chamber (1) exclusively by ferrostatic pressure upon immersion of at least part of the sample chamber in a molten metal in a direction such that the first end is immersed first, the inlet opening (6) has an open cross-sectional area which in comparison to the cross-sectional area of the sample chamber (1) directly behind the inlet opening (6), looking counter to the immersion direction, has a size such that the filling velocity of the sample chamber (1) based on ferrostatic pressure is not more than 1/5 of the filling velocity of an inlet opening corresponding to the cross-sectional area of the sample chamber (1) directly behind the inlet opening (6), that the inlet opening is slit-shaped, having an open cross-sectional area between 0.4 and 3 mm², with the smallest opening width of the inlet opening being at least 0.1 mm, and that the inlet opening (6) is arranged in such a way that the melt flows into the chamber (1) at an angle ($\alpha$) between 30 degrees and 150 degrees to the longitudinal axis of the sample chamber (1).

2. An immersion sampler according to claim 1 wherein said refractory material is quartz glass.

3. An immersion sampler according to claim 1 wherein the inlet opening (6) is so arranged that the melt flows into the chamber (1) counter to the immersion direction at an angle ($\alpha$) between 80 and 100 degrees.

4. An immersion sampler according to claim 1 wherein the immersion end of the sample chamber (1) has a cross-section narrowing in the immersion direction.

5. An immersion sampler according to claim 4 wherein the immersion end of the sample chamber (1) has a rounded off closure.

6. An immersion sampler according to claim 1 wherein the second end of sample chamber (1) is closed by an open-pored plug which covers the cross-sectional area of the second end of the sample chamber (1).

7. An immersion sampler according to claim 6 wherein the plug comprises molding sand.

* * * * *